United States Patent
Miyasato (10) Patent No.: US 10,390,706 B2
(45) Date of Patent: Aug. 27, 2019

(54) PHOTOACOUSTIC IMAGING APPARATUS, PHOTOACOUSTIC IMAGING METHOD, AND STORAGE MEDIUM

(75) Inventor: Takuro Miyasato, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 567 days.

(21) Appl. No.: 13/634,181

(22) PCT Filed: Mar. 14, 2011

(86) PCT No.: PCT/JP2011/056670
§ 371 (c)(1),
(2), (4) Date: Sep. 11, 2012

(87) PCT Pub. No.: WO2011/122382
PCT Pub. Date: Oct. 6, 2011

(65) Prior Publication Data
US 2013/0006088 A1 Jan. 3, 2013

(30) Foreign Application Priority Data
Mar. 29, 2010 (JP) .................. 2010-075662

(51) Int. Cl.
*A61B 5/00* (2006.01)
*A61B 8/00* (2006.01)
*G01N 21/17* (2006.01)

(52) U.S. Cl.
CPC .......... *A61B 5/0073* (2013.01); *A61B 5/0095* (2013.01); *A61B 8/00* (2013.01); *G01N 21/1702* (2013.01); *A61B 5/0091* (2013.01)

(58) Field of Classification Search
USPC ........................................................ 600/407
See application file for complete search history.

(56) References Cited

U.S. PATENT DOCUMENTS 5,673,114 A * 9/1997 Ushio ........................... 356/432
5,713,356 A 2/1998 Kruger
(Continued)

FOREIGN PATENT DOCUMENTS

CN 101453939 A 6/2009
CN 102843960 B 2/2015
(Continued)

OTHER PUBLICATIONS

Razansky et al., "Hybrid Photoacoustic Fluorescence Molecular Tomography Using Finite-Element-Based Inversion" Medical Physics, Oct. 2007, pp. 4293-4301, vol. 34, No. 11.
(Continued)

*Primary Examiner* — Jennifer Dieterle
(74) *Attorney, Agent, or Firm* — Canon U.S.A., Inc., IP Division (57) ABSTRACT

An optical property distribution, such as an absorption coefficient of the inside of a subject, is highly precisely acquired.

A photoacoustic imaging apparatus includes an acoustic converting unit configured to receive acoustic waves generated by irradiating a subject with emitted light and to convert the acoustic wave to an electrical signal; and a processing unit configured to determine a light intensity distribution inside the subject on the basis of a light intensity distribution or an illuminance distribution of the light incident on the surface of the subject and to generate image data on the basis of the electrical signal and the determined light intensity distribution inside the subject.

32 Claims, 9 Drawing Sheets

(56) References Cited

U.S. PATENT DOCUMENTS

| | | | |
|---|---|---|---|
| 5,781,294 A * | 7/1998 | Nakata et al. | 356/487 |
| 6,403,944 B1 | 6/2002 | MacKenzie et al. | |
| 2003/0225320 A1 | 12/2003 | Jeon et al. | |
| 2007/0187632 A1 * | 8/2007 | Igarashi | 250/559.36 |
| 2008/0221647 A1 * | 9/2008 | Chamberland et al. | 607/88 |
| 2008/0306371 A1 * | 12/2008 | Fukutani et al. | 600/407 |
| 2009/0005685 A1 * | 1/2009 | Nagae et al. | 600/459 |
| 2009/0105588 A1 * | 4/2009 | Emelianov et al. | 600/438 |
| 2010/0004875 A1 * | 1/2010 | Urano et al. | 702/40 |
| 2010/0056916 A1 * | 3/2010 | Bakker | A61B 5/0084 600/443 |
| 2010/0087733 A1 | 4/2010 | Nakajima et al. | |
| 2011/0106478 A1 | 5/2011 | Someda | |
| 2011/0142316 A1 * | 6/2011 | Wang | G06T 11/006 382/131 |

FOREIGN PATENT DOCUMENTS

| | | | | |
|---|---|---|---|---|
| JP | 2009-018153 A | 1/2009 | | |
| JP | 2010-017427 A | 1/2010 | | |
| JP | 2010-046215 A | 3/2010 | | |
| JP | 06016881 B2 | 10/2016 | | |
| KR | 20030075779 A | 9/2003 | | |
| WO | 9321818 A1 | 11/1993 | | |
| WO | WO 2008075961 A2 * | 6/2008 | | |
| WO | 2008/103982 A2 | 8/2008 | | |
| WO | 2009011934 A1 | 1/2009 | | |
| WO | WO 2009011934 A1 * | 1/2009 | | |
| WO | WO 2009158146 A2 * | 12/2009 | | A61B 5/0091 |
| WO | 2010/024290 A1 | 3/2010 | | |
| WO | 2010030043 A1 | 3/2010 | | |

OTHER PUBLICATIONS

Laufer et al., "Quantitative Spatially Resolved Measurement of Tissue Chromophore Concentration Photoacoustic Spectroscopy: application to the measurement of blood oxygenation and haemoglobin concentration" Jan. 2007, pp. 141-168, vol. 52 No. 1.

Mallidi et al., "Photoacoustic Technique to Measure Beam Profile of Pulsed Laser Systems" May 2009, pp. 54901-54901, vol. 80, No. 5.

Rosenthal et al., "Quantitative Optoacoustic Signal Extraction Using Spare Signal Representation" Dec. 2009, pp. 1997-2006, vol. 28 No. 12.

* cited by examiner

PHOTOACOUSTIC IMAGING APPARATUS, PHOTOACOUSTIC IMAGING METHOD, AND STORAGE MEDIUM

TECHNICAL FIELD

The present invention relates to a photoacoustic imaging apparatus, a photoacoustic imaging method, and a program to execute a photoacoustic imaging method.

BACKGROUND ART

Research on photoacoustic imaging apparatuses that acquire information about the inside of a subject by allowing light, such as a laser beam, emitted from a light source to enter and propagate through the subject has been actively carried out. In PTL 1, photoacoustic tomography (PAT) is proposed as such a photoacoustic imaging technique.

PAT is technique of visualizing information related to the optical characteristic of the inside of an organism, which is a subject, by irradiating the organism (subject) with pulsed light emitted from a light source, receiving an acoustic wave generated when the light that has propagated and diffused through the subject is absorbed by the organism's tissue, and analytically processing the received acoustic wave. In this way, information about biological information, such as an optical-characteristic-value distribution in the subject, and, particularly, an optical-energy-absorption density distribution can be acquired.

In PAT, an initial acoustic pressure $P_0$ of an acoustic wave generated from an optical absorber inside the subject can be represented by the following expression.

$$P_0 = \Gamma \cdot \mu_a \cdot \Phi \quad (1)$$

Here, $\Gamma$ represents the Grüneisen coefficient and is obtained by dividing the product of the isobaric volume expansion coefficient $\beta$ and the square of sonic speed c with isobaric specific heat $C_P$. $\Gamma$ is known to be a substantially constant value when the subject is specified, where $\mu_a$ represents an optical absorption coefficient of an absorber, and $\Phi$ represents the light intensity (which is the intensity of light incident on the absorber and is also referred to as optical fluence) in a local area.

The change over time of the acoustic pressure P, which is the volume of an acoustic wave propagated through the subject is measured, and an initial-acoustic-pressure distribution is calculated from the measured result. By dividing the calculated initial-acoustic-pressure distribution with the Grüneisen coefficient $\Gamma$, the distribution of the product of $\mu_a$ and $\Phi$, i.e., the optical-energy-absorption density distribution, can be acquired.

As represented by Expression 1, to acquire the distribution of the optical absorption coefficient $\mu_a$ from the distribution of the initial-acoustic-pressure distribution, it is necessary to determine the distribution of the light intensity $\Phi$ inside the subject. When an area sufficiently large with respect to the thickness of the subject is irradiated with a uniform amount of light, the distribution $\Phi$ of the light intensity in the subject can be presented by the following expression when light propagates through the subject as plane waves.

$$\Phi = \Phi_0 \cdot \exp(-\mu_{\mathit{eff}} \cdot d) \quad (2)$$

Here, $\mu_{\mathit{eff}}$ represents an average effective attenuation coefficient of the subject, and $\Phi_0$ represents the amount of light incident on the subject from a light source (the light intensity at the surface of the subject). Furthermore, d represents the distance between the area on the surface of the subject irradiated with the light emitted from the light source (light irradiation area) and the optical absorber in the subject.

By using the light intensity distribution $\Phi$ represented by Expression 2, the optical absorption-coefficient distribution ($\mu_a$) can be calculated from the optical-energy-absorption density distribution ($\mu_a \Phi$) of Expression 1.

CITATION LIST

Patent Literature

PTL 1 U.S. Pat. No. 5,713,356

SUMMARY OF INVENTION

Technical Problem

However, when the shape of the subject is not simple and/or when the amount of light emitted from a light source incident on the subject is not uniform, the area of the light irradiation area on the surface of the subject and the irradiation light intensity distribution are not uniform. Therefore, the light intensity in the subject is not uniform in the inner direction from the irradiated surface. Consequently, Expression 2 cannot be used. Thus, to precisely determine the optical-characteristic-value distribution in the subject, such non uniform properties need to be considered. The present invention highly precisely acquires an optical-characteristic-value distribution, such as an absorption coefficient of the inside of a subject.

Solution to Problem

The present invention provides a photoacoustic imaging apparatus including an acoustic converting unit configured to receive an acoustic wave generated by irradiating a subject with light emitted from a light source and to convert the acoustic wave to an electrical signal; and a processing unit configured to determine a light intensity distribution inside the subject on the basis of a light intensity distribution or an illuminance distribution of the light incident on the surface of the subject and to generate image data on the basis of the electrical signal and the determined light intensity distribution inside the subject.

The present invention also provides a method of photoacoustic imaging including the steps of generating image data from an electrical signal converted from an acoustic wave generated when light emitted from a light source is incident on a subject; determining a light intensity distribution or an illuminance distribution at a surface of the subject of the light emitted from a light source; determining a light intensity distribution of the inside of the subject on the basis of the light intensity distribution or the illuminance distribution at a surface of the subject; and generating image data on the basis of the electrical signal and the light intensity distribution of the inside of the subject.

Advantageous Effects of Invention

The present invention highly precisely acquires an optical property distribution, such as an absorption coefficient of the inside of a subject.

DESCRIPTION OF EMBODIMENTS

The present invention will be described below with reference to the drawings. In the present invention, acoustic waves include sonic waves, ultrasonic waves, and photoacoustic waves and are elastic waves that are generated inside a subject by irradiating the subject with light (electromagnetic waves), such as near infrared rays. The photoacoustic imaging apparatus according to the present invention is an apparatus that generates image data, which is to be used in diagnosis of malignant tumors and vascular diseases in human being and other animals and follow-up in chemotherapy, by acquiring biological information about the inside of the subject. The subject may be region in a human body or an animal body that is to be diagnosed, such as a breast, a finger, or a limb. An optical absorber inside a subject is a part of the subject that has a relatively high absorption coefficient. In case the subject is a human body, the optical absorber is, for example, a malignant tumor, which has many blood vessels or new blood vessels containing oxygenated and/or reduced hemoglobin.

First Embodiment

Figure 1A:
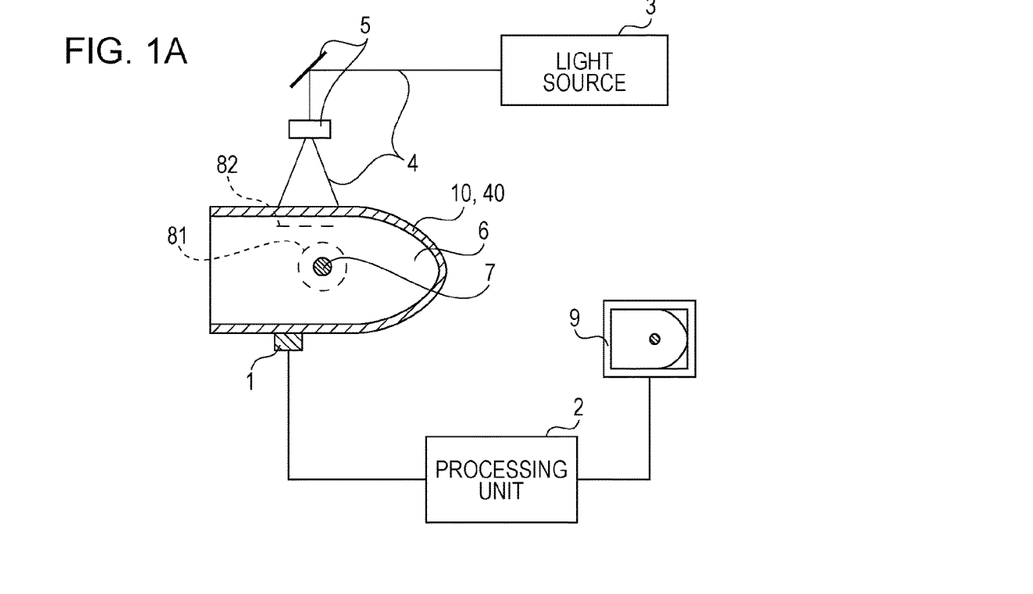
FIGS. 1A and 1B are schematic views of a photoacoustic imaging apparatus according to exemplary embodiments of the present invention.

FIG. 1A illustrates a photoacoustic imaging apparatus according to this embodiment. The photoacoustic imaging apparatus according to this embodiment includes an acoustic converting unit 1 and a processing unit 2. Furthermore, in this embodiment, an acoustic-wave generating member 10 is provided along the face of a subject 6. The acoustic-wave generating member 10 has an absorption coefficient different from that of the subject 6. The thickness, optical absorption coefficient, and Grüneisen coefficient of the acoustic-wave generating member 10 are measured in advance. A light beam 4 emitted from a light source 3 is incident on the subject 6, which is, for example, an organism, via an optical system 5, including a lens, a mirror, and an optical fiber. When part of the optical energy propagated through the subject 6 is absorbed by an optical absorber 7 (which is a sound source), such as the interior of a blood vessel or blood, thermal expansion of the optical absorber 7 generates an acoustic wave 81 (which is typically an ultrasonic wave). An acoustic wave 82 is generated at the acoustic-wave generating member 10 in response to receiving the light beam 4 emitted from the light source 3. The acoustic waves 81 and 82 are received by the acoustic converting unit 1 and are converted to electrical signals. Then, the processing unit 2 generates image data, such as an optical-characteristic-value distribution, of the subject 6 on the basis of the electrical signals and a light intensity distribution of light emitted from the light source 3 incident on the surface of the subject 6 (hereinafter referred to as "surface-light-intensity distribution"). Specifically, the light intensity distribution in the subject 6 (hereinafter referred to as "internal-light-intensity distribution") is determined by the processing unit 2 on the basis of the surface-light-intensity distribution, and image data is generated on the basis of the electrical signals and the internal-light-intensity distribution. Then, the image data is displayed as an image on a display device 9, such as a liquid crystal display. The photoacoustic imaging apparatus may include securing members 11, such as those illustrated in FIG. 1B, to secure the subject 6. The securing members 11 define part of the shape of the subject 6. Although not mentioned in particular, the other embodiments may also include such securing members.

Figure 2:
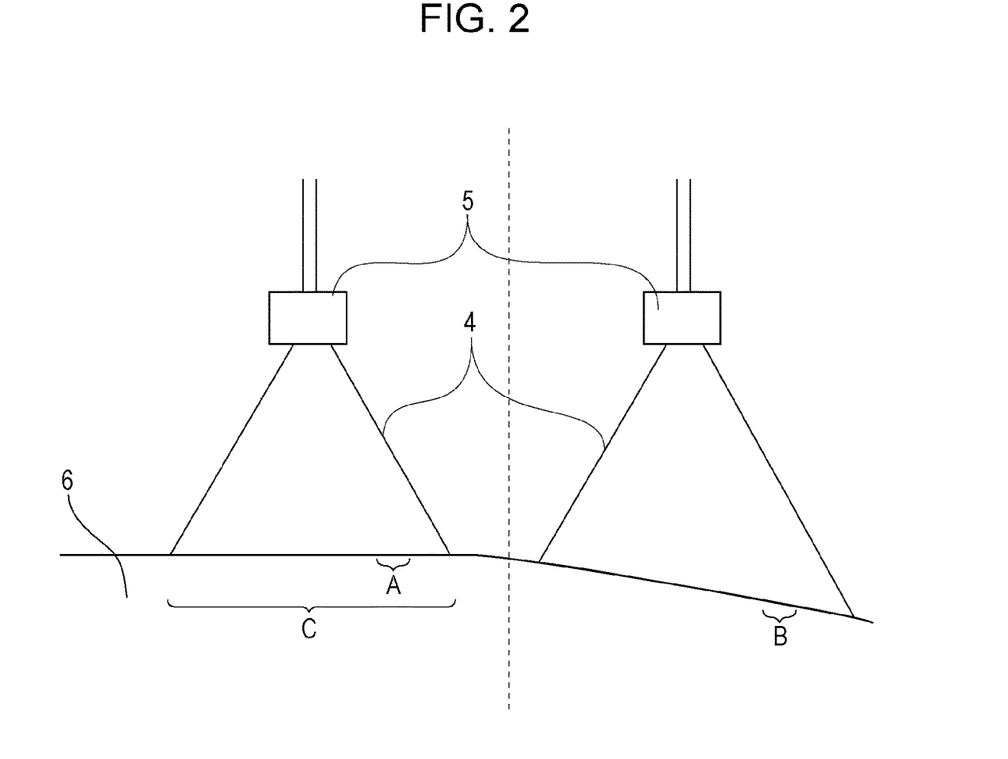
FIG. 2 is a schematic diagram illustrating a program to be solved by the present invention.

The optical absorbers 7 having the same shape, size, and absorption coefficient but being present at different positions in the subject 6 are displayed with different luminance and color in images of optical-energy-absorption density distribution and optical-absorption-coefficient distribution. This is because the number of photons that reach each optical absorber 7, i.e., the local amount of light in the subject 6, differs. The local amount of light inside the subject 6 may differ due to the influence of the surface-light-intensity distribution of the subject 6. FIG. 2 illustrates two areas (A and B) on the subject 6 having the same size being irradiated with light emitted from light sources that emit light of the same intensity. With reference to FIG. 2, even though the intensities of the light emitted from the light sources are the same, the illuminance at the areas A and B on the surface of the subject 6 differs because the size of the light irradiation areas differs. When the light from the light source 3 or the light beam 4 incident on the subject 6 via the optical system 5 diverge finitely and when the light intensity distribution is not uniform in the diverging direction, the illuminance differs within a light irradiation area (area C) depending on the position. Expression 2 can be applied when the emitted light intensity (surface-illuminance distribution) is uniform. However, such as in the above-described case, when the light intensity is not uniform, Expression 2 cannot be applied. According the present invention, by correcting the light intensity distribution in the subject using the surface-illuminance distribution of light emitted from a light source incident on a subject, optical absorbers having the same shape, size, and absorption coefficient can be displayed with substantially the same luminance and/or color.

Figure 1B:
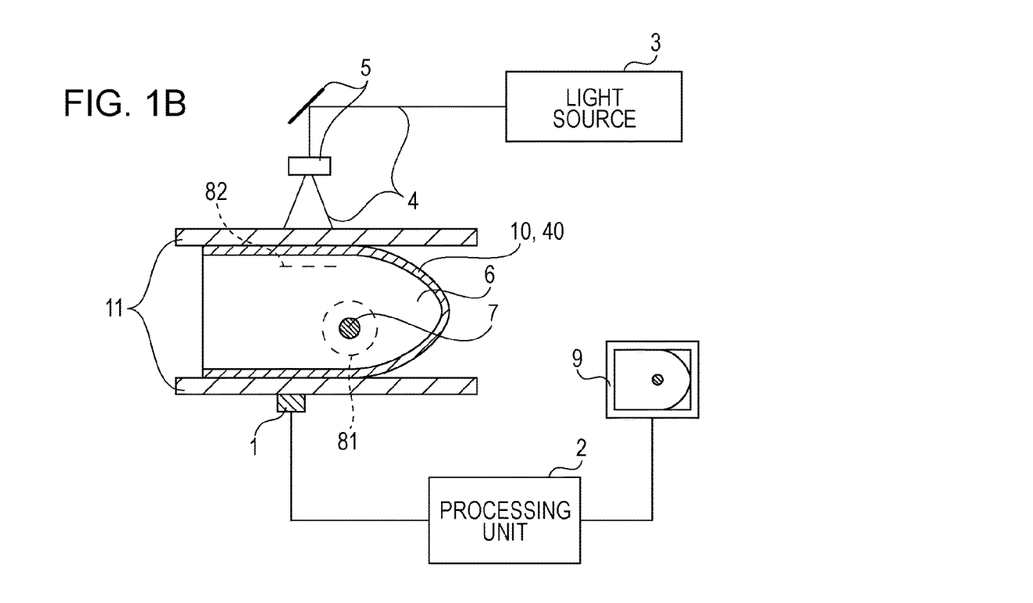
Figure 3:
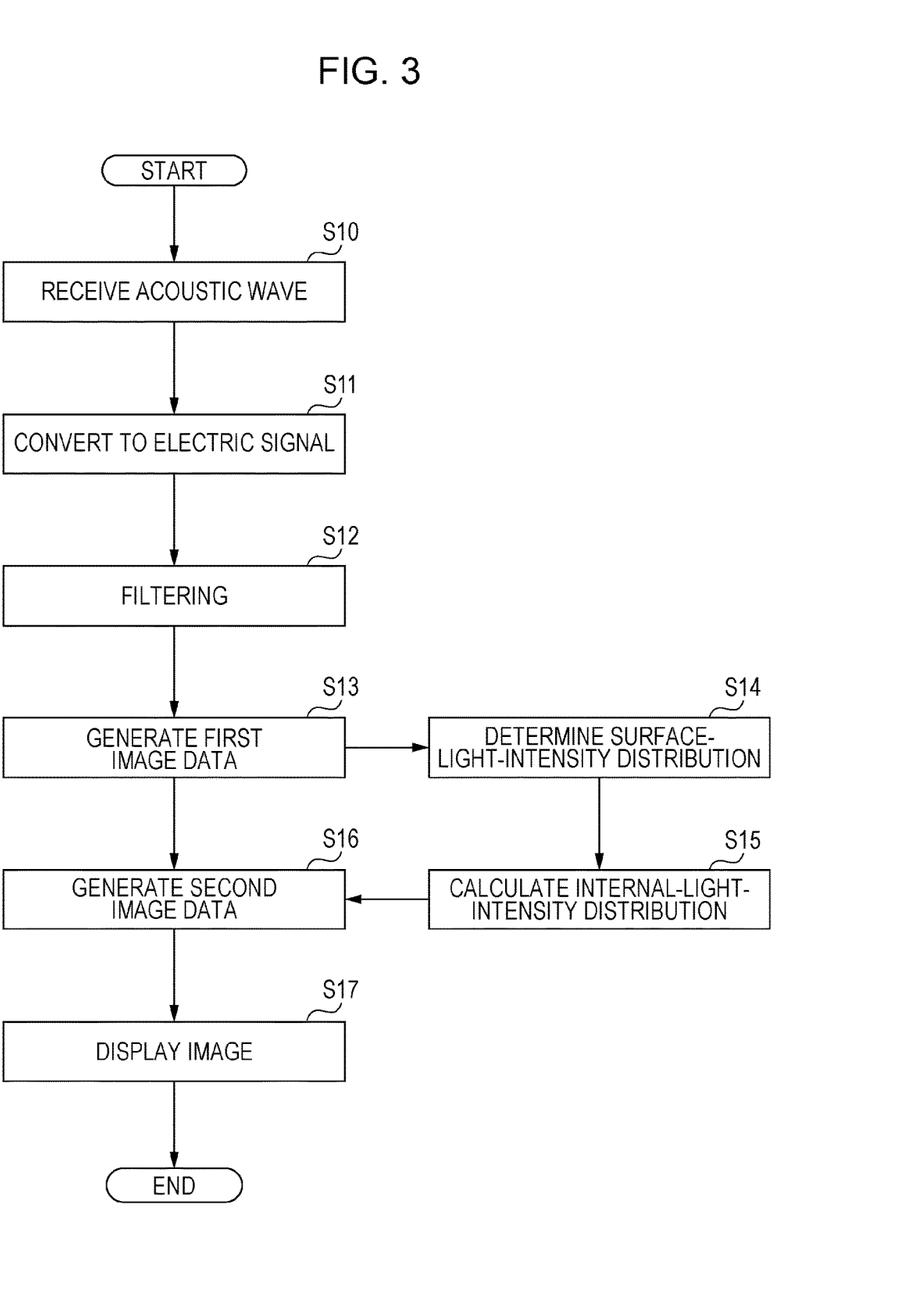
FIG. 3 is a flow chart illustrating a process carried out by the photoacoustic imaging apparatus according to the first embodiment of the present invention.

Next, the operation of the photoacoustic imaging apparatus according to this embodiment will be described with reference to FIGS. 1 and 3.

The subject 6 is irradiated with the light beam 4 from the light source 3, and the acoustic converting unit 1 receives the acoustic wave 81 generated at the optical absorber 7 in the subject 6 and the acoustic wave 82 generated at the acoustic-wave generating member 10 disposed on the surface of the subject 6 (S10). The received acoustic waves are converted to electrical signals at the acoustic converting unit 1 (S11) and are sent to the processing unit 2. The processing unit 2 performs amplification, A/D conversion, and filtering on the electrical signals (S12), calculates the position and size of the optical absorber 7 or biological information, such as the initial-acoustic-pressure distribution, and generates first image data (S13).

The processing unit 2 determines the surface-illuminance distribution of the light from the light source 3 incident on the subject 6 on from the first image data acquired from the electrical signals (S14). This is described below.

The acoustic wave 81 is generated in response to light propagated through and attenuated inside the subject 6, whereas the acoustic wave 82 is generated at the surface of the subject 6 in response to light that is substantially not attenuated. The acoustic-wave generating member 10 has an absorption coefficient larger than that of the subject 6. Therefore, the acoustic wave 82 generated at the surface of the subject 6 has a larger volume than that of the acoustic wave 81 generated in the optical absorber 7. Thus, a part having an initial acoustic pressure greater than the other parts can be extracted from the first image data acquired in Step S13 (initial-acoustic-pressure distribution $P_0$). The extracted part corresponds to a line between the subject 6 and the acoustic-wave generating member 10, i.e., the surface of the subject 6. Specifically, the line connecting parts having an initial acoustic pressure greater than a predetermined threshold defines the line between the subject 6 and the acoustic-wave generating member 10. The surface of the subject 6 is determined, and the initial-acoustic-pressure distribution ($\Gamma_b \mu_b \Phi_0$) along the line can be obtained. $\Gamma_b$ represents a Grüneisen coefficient of the acoustic-wave generating member 10 and $\mu_b$ presents the absorption coefficient of the acoustic-wave generating member 10. The surface-illuminance distribution $\Phi_0$ of the light emitted from the light source 3 and incident on the subject 6 can be calculated by subtracting the coefficients $\Gamma_b$ and $\mu_b$ from the initial-acoustic-pressure distribution ($\Gamma_b \mu_b \Phi_0$) along the line.

Then, the internal-light-intensity distribution $\Phi$ in the subject 6 is determined on the basis of the surface-illuminance distribution $\Phi_0$ (S15). Specifically, using the shape of the surface of the subject 6 and the surface-illuminance distribution of the subject 6 acquired in Step S14, an imaginary light source having a light intensity distribution that is the same as the surface-illuminance distribution $\Phi_0$ is disposed on the surface of the subject 6 in a numerical space to calculate the internal-light-intensity distribution $\Phi$ in the subject 6. At this time, the internal-light-intensity distribution is calculated using a diffusion equation and a transport equation.

The processing unit 2 generates second image data, such as the absorption-coefficient distribution, on the basis of the internal-light-intensity distribution $\Phi$ determined in Step S15 and the first image data (initial-acoustic-pressure distribution $P_0$) acquired in Step S13 (S16). By using the internal-light-intensity distribution determined in S15 by Expression 1, the absorption-coefficient distribution can be calculated. An image based on the second image data acquired in this way is displayed on the display device 9 (S17).

Next, the configuration of the photoacoustic imaging apparatus according to this embodiment will be described in detail below.

The acoustic converting unit 1 includes at least one element that converts acoustic waves to electrical signals, transducers using a piezoelectric phenomenon, resonance of light, and/or change in capacitance. Any type of element may be used so long as it is capable of converting acoustic waves into electrical signals. By one- or two-dimensionally arranging a plurality of acoustic-wave receiving elements, photoacoustic waves can be received simultaneously at different sites. Thus, reception time can be reduced, and the influence of vibration of the subject can be reduced. By moving one of the elements, it is possible to receive the same signal as that received when the elements are arranged one- or two-dimensionally. It is desirable to apply acoustic matching material, such as gel, between the acoustic converting unit 1 and the subject 6 in order to improve the acoustic matching.

A work station is typically used as the processing unit 2, and image reconstruction (generation of image data) is performed using preprogrammed software. For example, the software used at the work station includes processing of determining the light intensity distribution or the illuminance distribution on the surface of the subject from electrical signals from the photoacoustic imaging apparatus or an external unit and a signal processing module for noise reduction. Furthermore, the software used at the work station includes an image reconstruction module for image reconstruction. In PAT, normally, as preprocessing of image reconstruction, noise reduction is performed on signals received at different sites. It is desirable that such preprocessing is performed by the signal processing modules. The image reconstruction module forms image data by image reconstruction, and as an image reconstruction algorithm, for example, backprojection in a time domain or a Fourier domain, which is typically used in tomography techniques, is applied. Image data is two- and three-dimensional data about biology information. Two-dimensional data is constituted of multiple data sets of pixel data, and three-dimensional data is constituted of multiple data sets of voxel data. Pixel data and voxel data are obtained through image reconstruction of acoustic waves acquired at multiple sites. Three-dimensional image data will be described below. However, the present invention can also be applied to two-dimensional image data.

The light source 3 emits light having a predetermined wavelength that is absorbed by a predetermined component (e.g., hemoglobin) that constitutes an organism. Specifically, the wavelength of the light is preferably 500 nm or greater and 1,200 nm or smaller. This is because, in the processing described below, it is easier to distinguish between the acoustic waves generated at the surface of the subject (for example, at the skin) and the acoustic waves generated at an optical absorber inside the subject (for example, hemoglobin). At least one light source 3 capable of generating pulsed light between 5 and 50 ns is provided. Laser, which has larger power, is desirable as the light source 3. However, instead of laser, a light-emitting diode may be used. Various different types of laser, such as solid-state laser, gas laser, dye laser, and semiconductor laser, can be used. The light may be emitted from the side of the acoustic converting unit 1 or from the opposite side. Furthermore, the light may be emitted from both sides of the subject 6.

The optical system 5 includes mirrors that reflect light and lenses that converge, diverge, and change the shape of light. The optical system 5 may include, in addition to the mirrors and lenses, optical waveguides and have any configuration so long as the light emitted from the light source 3 is incident on the subject 6 in a desired shape. It is desirable that the light be converged by a lens to irradiate a predetermined area. It is also desirable that the area on the subject 6 irradiated by light be movable. In other words, it is desirable that the light emitted from the light source 3 be movable on the subject 6. Movable light allows a larger area to be irradiated with light. It is even more desirable that the area on the subject 6 irradiated by light move in synchronization with the acoustic converting unit 1. Methods of moving an area on the subject 6 irradiated with light include a method using a movable mirror and a method of mechanically moving the light source 3.

Figure 4A:
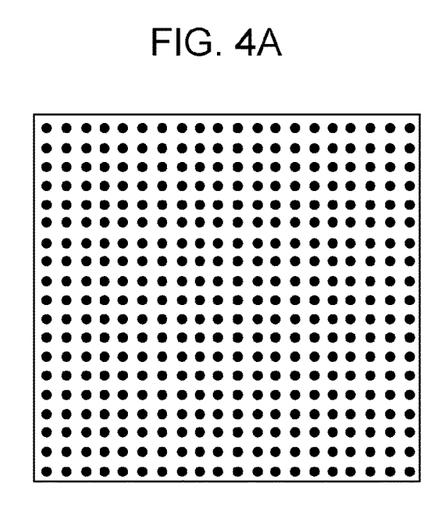
FIGS. 4A and 4B are schematic views of acoustic-wave generating members included in the photoacoustic imaging apparatus according to exemplary embodiments of the present invention.
Figure 4B:
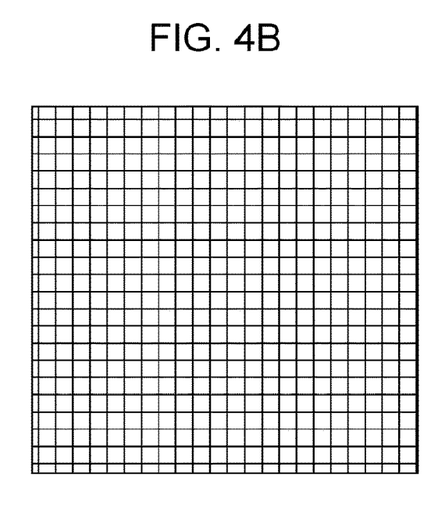

The acoustic-wave generating member 10 has a predetermined absorption coefficient, is disposed on the surface of the subject 6, and has known thickness, optical absorption coefficient, and Grüneisen coefficient. The acoustic-wave generating member 10 generates acoustic waves by absorbing light emitted from the light source 3 and is capable of calculating the surface shape and the surface-light-intensity distribution of the subject 6. The acoustic-wave generating member 10 is made of a material having an absorption coefficient of the light generating an acoustic wave greater than the average absorption coefficient of the subject 6. Specifically, it is desirable that the optical absorption coefficient be 0.005 $mm^{-1}$ or greater and 0.100 $mm^{-1}$ or smaller. When the absorption coefficient is greater than 0.100 $mm^{-1}$, the amount of light entering the subject 6 decreases, and thus, the acoustic wave generating inside the subject 6 is small. In contrast, when the absorption coefficient is smaller than 0.005 $mm^{-1}$, this is smaller than the average absorption coefficient of the inside of the subject 6; therefore, it is difficult to distinguish between the acoustic waves from the inside and the surface of the subject 6, and thus it is difficult to calculate the surface shape of the subject 6. It is desirable that the optical absorption coefficient is 0.010 $mm^{-1}$ or greater and 0.080 $mm^{-1}$ or smaller. It is desirable to use a material having a Grüneisen coefficient greater than or equal to 0.8 and smaller than or equal to 1.5. The average Grüneisen coefficient of the subject 6 is approximately 0.5. The acoustic-wave generating member 10 include absorber particles having a known absorption coefficient disposed as a spotty film, as illustrated in FIG. 4A, or may include absorbers arranged in a grid, as illustrated in FIG. 4B. Instead, the acoustic-wave generating member 10 may include absorber fine particles disposed as a uniform film. It is possible to use an acoustic matching material having a known absorption coefficient, such as a gel, as the acoustic-wave generating member 10.

Second Embodiment

The photoacoustic imaging apparatus according to this embodiment differs from the photoacoustic imaging apparatus according to the first embodiment in that the acoustic-wave generating member 10 is not provided. In this embodiment, the surface shape is calculated using an acoustic wave that is generated due to the discontinuity in the optical characteristics (for example, absorption coefficients) of the subject 6 and the surroundings. Then, the illuminance distribution (hereinafter referred to as "surface-illuminance distribution") at the surface of the subject 6 is calculated on the basis of the calculation result of the surface shape and the intensity distribution of the light emitted from the light source 3. An example in which air surrounds the subject 6 will be described below, but this embodiment is not limited thereto.

The absorption coefficients and the Grüneisen coefficients of air and the subject 6 are discontinuous. Therefore, light is absorbed at the surface therebetween, i.e., the surface of the subject 6, and, as a result, an acoustic wave 82 is generated at the surface of the subject 6. The acoustic converting unit 1 receives an acoustic wave 81 generated at the optical absorber 7 and the acoustic wave 82 and converts these acoustic waves to electrical signals.

Figure 5:
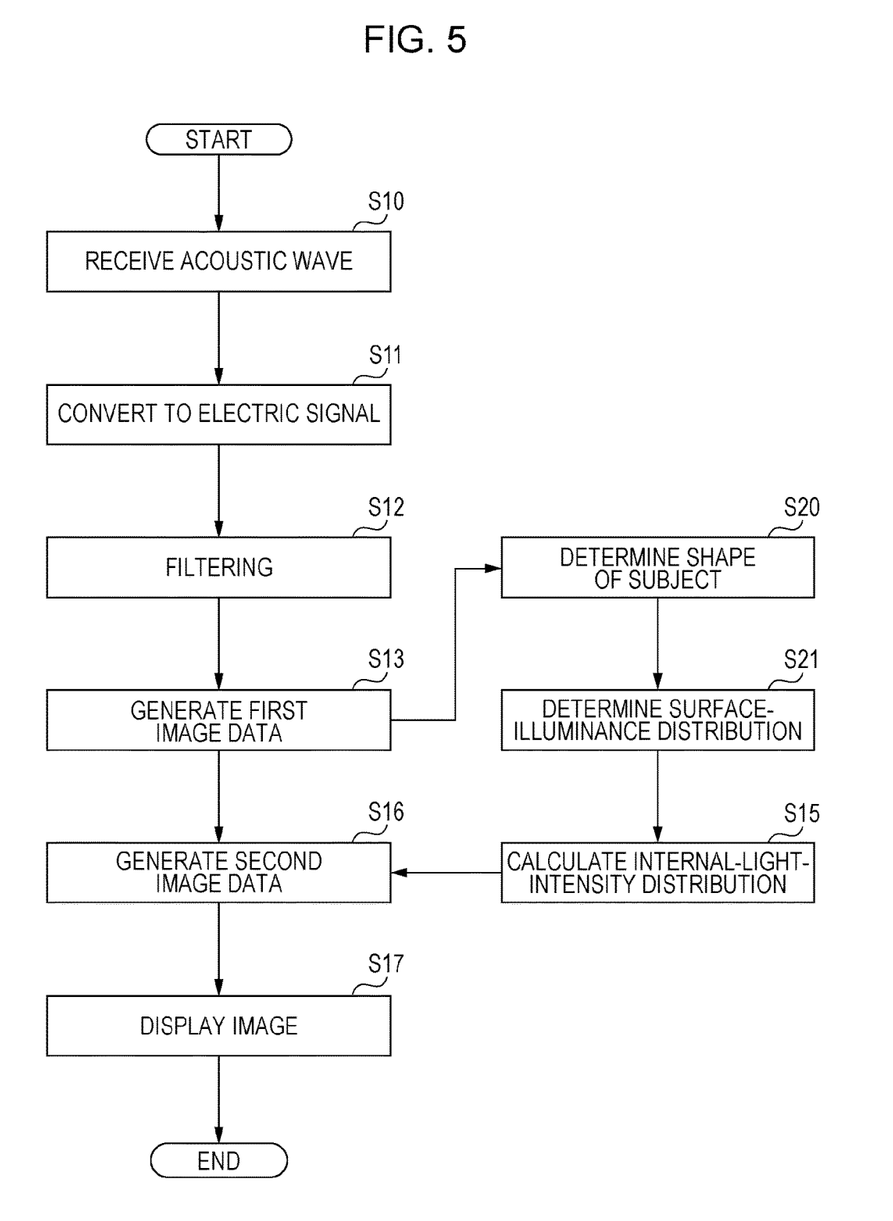
FIG. 5 is a flow chart illustrating a process carried out by the photoacoustic imaging apparatus according to the second embodiment of the present invention.

Next, the operation of the photoacoustic imaging apparatus according to this embodiment will be described with reference to FIG. 5. The acoustic wave 81 generated at the optical absorber 7 inside the subject 6 and the acoustic wave 82 generated at the surface of the subject 6 as a result of irradiating the subject 6 with the light beam 4 are received by the acoustic converting unit 1 (S10). The received acoustic wave 81 is converted to an electrical signal at the acoustic converting unit 1 (S11) and is received by the processing unit 2. After performing filtering on the electrical signal (S12), the processing unit 2 calculates biological information such as the position and size of the optical absorber 7 or biological information, such as the initial-acoustic-pressure distribution, to generate a first image data (S13).

The processing unit 2 determines the shape of the subject 6 on the basis of the first image data acquired from the electrical signal (S20). This is described below.

Since the acoustic wave 82 generated at the surface of the subject 6 is generated by receiving light that is substantially not attenuated, the acoustic wave 81 is larger than the acoustic wave 81 generated at the optical absorber 7. Thus, a part having an initial acoustic pressure greater than the other parts can be extracted from the first image data acquired in Step S13 (initial-acoustic-pressure distribution $P_0$). The extracted part corresponds to the boundary between the subject 6 and the acoustic-wave generating member 10, i.e., the surface of the subject 6. Specifically, the line obtained by connecting the parts having an initial acoustic pressure greater than a predetermined threshold defines the boundary between the subject 6 and the acoustic-wave generating member 10.

When the absorption (absorption coefficient) at the boundary between the subject 6 and air (surroundings of the subject 6) is known, similar to the first embodiment, the surface-illuminance distribution of the light emitted from the light source 3 incident on the subject 6 can be calculated from the initial-acoustic-pressure distribution at the boundary.

When the absorption (absorption coefficient) at the boundary between the subject 6 and air (surroundings of the subject 6) is not known, the surface-illuminance distribution the light emitted from the light source 3 incident on the subject 6 cannot be calculated from the initial-acoustic-pressure distribution at the boundary; thus, the following process is carried out.

The processing unit 2 determines the surface-illuminance distribution of the light beam 4 emitted from the light source 3 incident on the subject 6 on the basis of the shape of the subject 6 and the intensity distribution of the light beam 4 emitted from the light source 3 (S21). This is described below.

Figure 6:
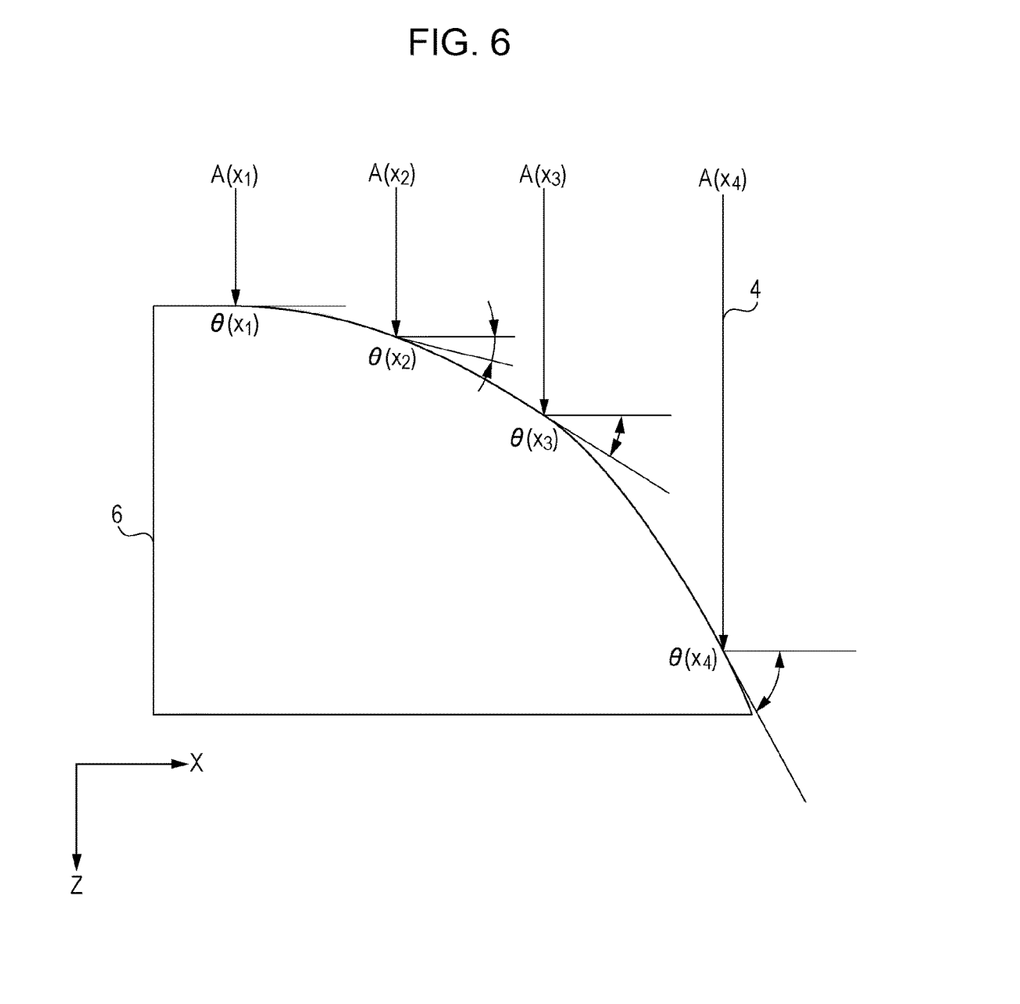
FIG. 6 is a schematic view illustrating a process of determining an illuminance distribution at the surface, which is Step 21 in FIG. 5.

The intensity distribution of the light beam 4 emitted from the light source 3, which is a light intensity distribution in the inner direction orthogonal to the depth direction of the subject 6, is measured in advance. This is described below with reference to FIG. 6. With reference to FIG. 6, the shape of the subject 6 is represented by positions z in the depth direction of the subject 6, positions x in an inner direction orthogonal to the depth direction of the subject 6, and the inclination $\theta(x)$ to the surface. The light intensity distribution of the light beam 4 in the inner direction orthogonal to the depth direction of the subject 6 is presented by $A(x)$. It is presumed that light travels linearly outside the subject 6. The inclination distribution $\theta(x)$ of the light beam 4 on the surface of the subject 6 irradiated with light can be calculated with reference to the normal direction, which is calculated from the surface shape of the subject 6. By multiplying the light intensity distribution A(x) with cos θ(x) at each of the positions x and z, the surface-illuminance distribution of the subject 6 can be calculated.

In the example described above, light is presumed to travel linearly outside the subject 6. However, it is also possible to determine the surface-illuminance distribution by determining the propagation of the light beam 4 outside the subject 6 to the surface of the subject 6 using the light transport equation or the Monte Carlo simulation for light propagation.

Based on the surface-illuminance distribution, the internal-light-intensity distribution in the subject 6 is determined (S15). Specifically, using the shape of the surface of the subject 6 acquired in S20 and the surface-illuminance distribution of the subject 6 acquired in Step S21, an imaginary light source having a light intensity distribution that is the same as the surface-illuminance distribution is disposed on the surface of the subject 6 in a numerical space to calculate the internal-light-intensity distribution. At this time, the internal-light-intensity distribution is calculated using the light diffusion equation, the transport equation, or the Monte Carlo simulation for light propagation.

The processing unit 2 generates second image data, such as the absorption-coefficient distribution, on the basis of the internal-light-intensity distribution determined in Step S15 and the first image data acquired in Step S13 (S16). By using the internal-light-intensity distribution determined in S15 by Expression 1, the absorption-coefficient distribution can be calculated. An image based on the second image data acquired in this way is displayed on the display device 9 (S17).

Third Embodiment

Figure 7:
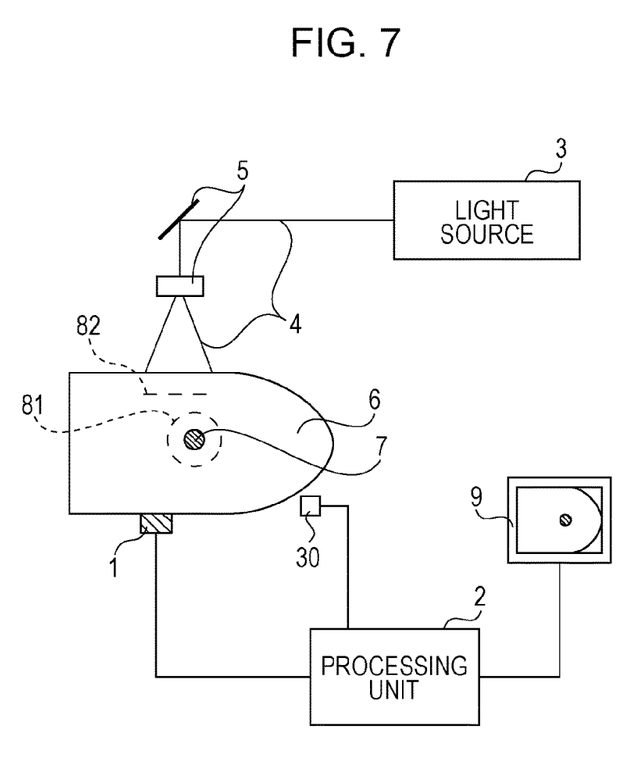
FIG. 7 is a schematic view of a photoacoustic imaging apparatus according to the third embodiments of the present invention.

FIG. 7 illustrates a photoacoustic imaging apparatus according to the third embodiment of the present invention. This embodiment differs from the second embodiment in that a measuring unit 30 is provided. The other configurations are the same as that of the second embodiment. The measuring unit 30 measures the shape of a subject 6.

As the measuring unit 30, an image pickup device, such as a CCD camera, can be used. In such a case, the processing unit 2 determines the shape of the subject 6 by calculating the outer shape and thickness of the subject 6 from the taken-in image. The measuring unit 30 may instead be an acoustic-wave converting unit (so-called ultrasonic-wave-echo acoustic converting unit) that transmits and receives acoustic waves. The acoustic converting unit 1 may function as the measuring unit 30, or the measuring unit 30 may be provided separately.

Figure 8:
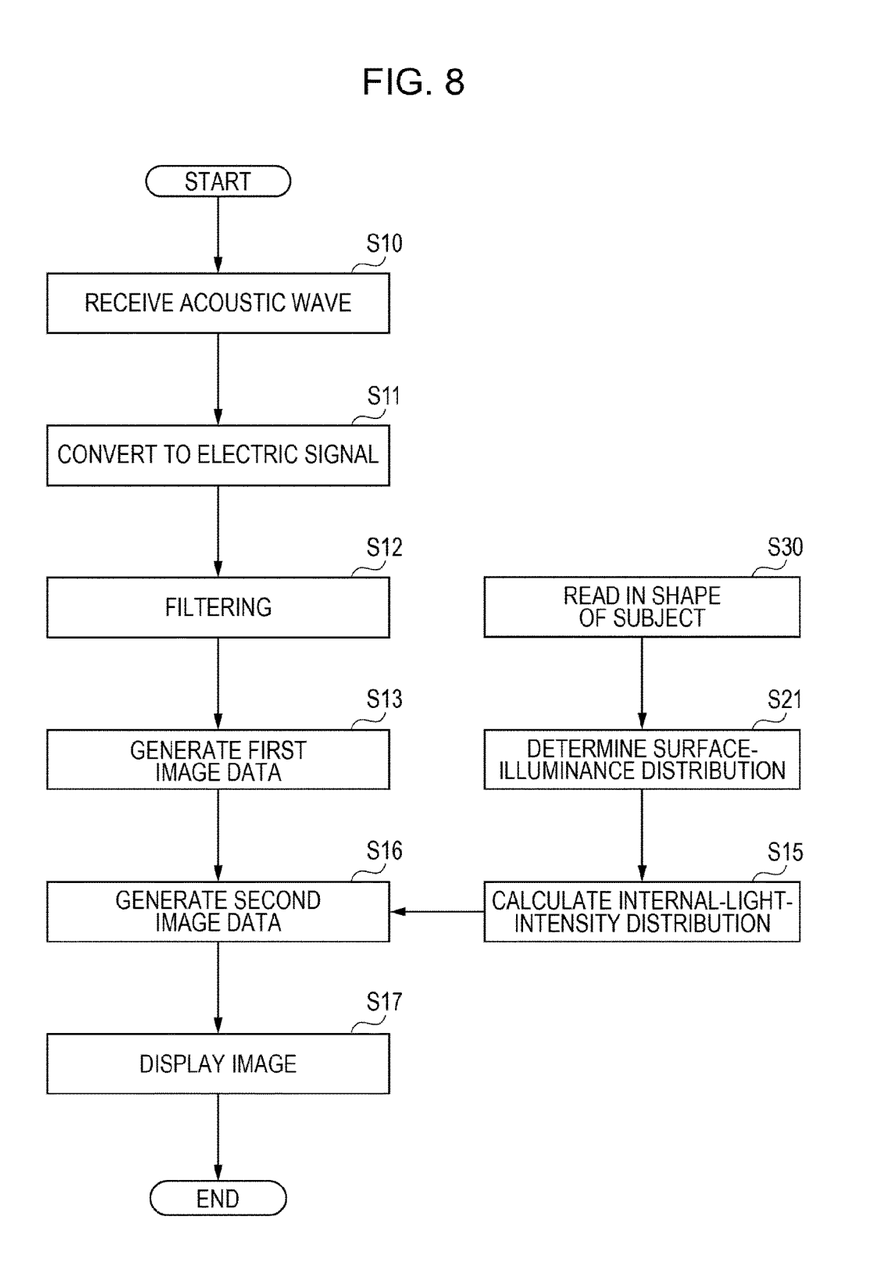
FIG. 8 is a flow chart illustrating a process carried out by the photoacoustic imaging apparatus according to the third embodiment of the present invention.

Next, with reference to FIG. 8, the operation of the photoacoustic imaging apparatus according to this embodiment of the present invention will be described. In the second embodiment, the shape of the subject 6 is determined from electrical signals (first image data) (S20). The operation of the photoacoustic imaging apparatus according to this embodiment differs in that the shape of the subject 6 is determined from an image of the subject 6 acquired by the measuring unit 30 (S30). The other operations are the same as those of the second embodiment.

Fourth Embodiment

The photoacoustic imaging apparatus according to this embodiment will be described with reference to FIGS. 1A and 1B. The photoacoustic imaging apparatus according to this embodiment includes a container 40 defining the shape of the subject 6 instead of the acoustic-wave generating member 10 in the photoacoustic imaging apparatus according to the first embodiment. The other configurations are the same as that of the first embodiment.

In this embodiment, since the shape of the subject 6 is uniquely determined, the surface-illuminance distribution of the light beam 4 emitted from the light source 3 incident on the surface of the subject 6 is uniquely determined. Specifically, the container 40 suitable for the subject 6 is selected from a plurality of containers having different shapes and sizes, and then the subject 6 is placed into the container 40 to perform PAT measurement.

The surface-illuminance distribution of the light incident on the surface of the subject 6 for each container is determined in advance and is stored in the processing unit 2 as a surface-illuminance distribution data table containing the surface-illuminance distribution data of the subject 6 for each container. The data table is prepared such that when a container is selected, the corresponding surface-illuminance distribution data of the subject 6 for the selected container is retrieved. Instead of providing a plurality of containers, a single container of which the capacity, size, and/or shape are changeable may be provided. In such a case, the surface-illuminance distributions of the light incident on the surface of the subject 6 when the size and/or shape of the container is changed in various ways may be determined in advance, and a surface-illuminance distribution data table containing the surface-illuminance distribution data for when the size and/or shape of the container is changed may be stored in the processing unit 2.

Figure 9:
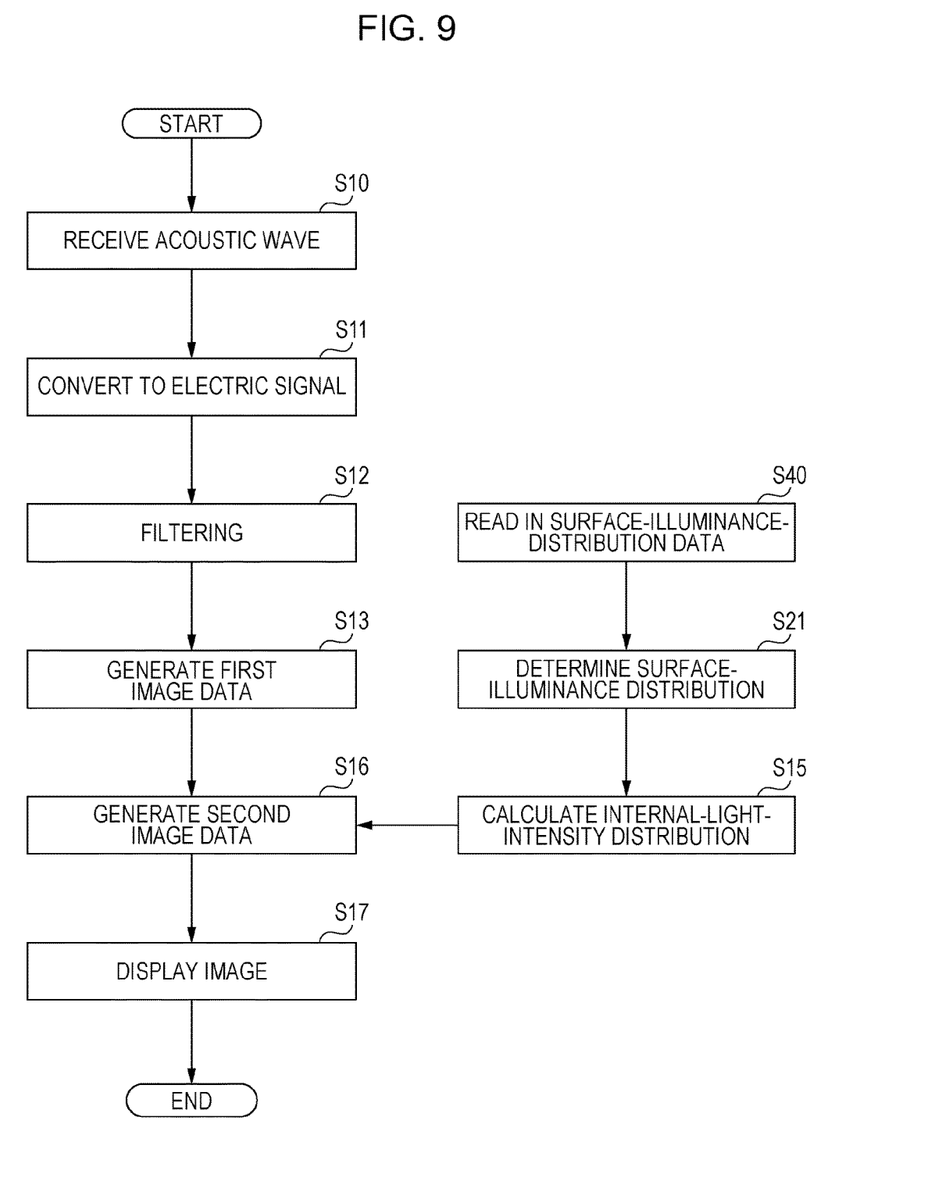
FIG. 9 is a flow chart illustrating a process carried out by the photoacoustic imaging apparatus according to the fourth embodiment of the present invention.

Next, the operation of the photoacoustic imaging apparatus according to this embodiment will be described with reference to FIG. 9. First, the container 40 is selected from a plurality of containers on the basis of the size and shape of the subject 6, and the subject 6 is placed into the container 40.

Then, the subject 6 is irradiated with the light beam 4 emitted from the light source 3, and the acoustic converting unit 1 receives the acoustic wave 81 generated at the optical absorber 7 inside the subject 6 (S10). The received acoustic wave 81 is converted to an electrical signal at the acoustic converting unit 1 (S11) and is received by the processing unit 2. After performing filtering on the electrical signal (S12), the processing unit 2 calculates the position and size of the optical absorber 7 or biological information such as the initial-acoustic-pressure distribution to generate first image data (image reconstruction, S13).

The processing unit 2 selects and reads in the surface-illuminance distribution data corresponding to the selected container 40 from the surface-illuminance distribution data table stored in the processing unit 2 (S40) and determines the surface-illuminance distribution of the light beam 4 emitted from the light source 3 incident on the subject 6 (S21).

Based on the surface-illuminance distribution, the internal-light-intensity distribution in the subject 6 is determined (S15). Specifically, using the shape of the subject 6 defined by the container 40 and the surface-illuminance distribution of the subject 6 acquired in Step S21, an imaginary light source having a light intensity distribution that is the same as the surface-illuminance distribution is disposed on the surface of the subject 6 in a numerical space to calculate the internal-light-intensity distribution. At this time, the internal-light-intensity distribution is calculated using the light diffusion equation, the transport equation, or the Monte Carlo simulation for light propagation.

The processing unit 2 generates second image data, such as the absorption-coefficient distribution, on the basis of the internal-light-intensity distribution determined in Step S15 and the first image data acquired in Step S13 (S16). By using the internal-light-intensity distribution determined in S15 by Expression 1, the absorption-coefficient distribution can be calculated. An image based on the second image data acquired in this way is displayed on the display device 9 (S17).

When light diffusion within the subject 6 can be predicted, an internal-light-intensity-distribution data table corresponding to the inside of the subject 6 may be used instead of the surface-illuminance distribution data table. In such a case, in Step S40, internal-light-intensity-distribution data is read in instead of the surface-illuminance distribution data, and Step S21 may be combined with Step S40.

Fifth Embodiment

The present invention may also be realized by the following processing. Software (program) that realizes the functions of the above-described first to fourth embodiments is applied to a system or an apparatus via a network or various storage media, and the program is read out by the system or a computer (CPU or MPU) of the apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-075662, filed Mar. 29, 2010 which is hereby incorporated by reference herein in its entirety.

REFERENCE SIGNS LIST 1 acoustic converting unit
2 processing unit
3 light source
4 light beam emitted from the light source
6 subject
81, 82 acoustic wave

The invention claimed is:

1. A method for acquiring subject information comprising the steps of:
   acquiring first image data by using an electrical signal acquired by converting an acoustic wave generated by irradiating a subject with light;
   acquiring a surface-illuminance distribution of the light incident on a surface of the subject by using information about a surface shape of the subject and an intensity distribution of light for irradiation to the subject;
   setting, on the surface of the subject in a numerical space, an imaginary light source having a light intensity distribution that is the same as the surface-illuminance distribution;
   acquiring an internal light intensity distribution inside the subject by calculating light propagation inside the subject in the numerical space, of light emitted from the imaginary light source; and
   acquiring second image data based on the first image data and the internal light intensity distribution inside the subject.

2. The method according to claim 1, further comprising measuring the surface shape of the subject.

3. The method according to claim 1, further comprising acquiring the information about the surface shape of the subject by using the electrical signal.

4. The method according to claim 3, further comprising acquiring third image data by using the electrical signal and acquiring the surface shape of the subject by using the third image data.

5. The method according to claim 1, further comprising:
   securing the subject with a securing member; and
   acquiring the information about the surface shape of the subject by using information about the securing member.

6. The method according to claim 1, further comprising acquiring the surface-illuminance distribution at the surface of the subject by selecting from a plurality of stored data items corresponding to the illuminance distribution at the surface of the subject.

7. The method according to claim 1, further comprising displaying an image on a display unit based on the second image data.

8. A non-transitory computer-readable storage medium storing a program configured to instruct a computer to execute the steps of a method for acquiring subject information, comprising:
   acquiring first image data by using an electrical signal acquired by converting an acoustic wave generated by irradiating a subject with light;
   acquiring a surface-illuminance distribution of incident light on a surface of the subject by using information about the surface shape of the subject and an intensity distribution of light for irradiation to the subject;
   setting, on the surface of the subject in a numerical space, an imaginary light source having a light intensity distribution that is the same as the surface-illuminance distribution;
   acquiring an internal light intensity distribution inside the subject by calculating light propagation inside the subject in the numerical space, of light emitted from the imaginary light source, and
   acquiring second image data based on the first image data and the internal light intensity distribution inside the subject.

9. A subject information acquisition apparatus comprising:
   an acoustic-wave converting unit configured to convert an acoustic wave generated by irradiating a subject with light into an electrical signal; and
   a processing unit configured to:
   acquire information about an inclination distribution of a surface of the subject for incident light onto the surface of the subject,
   acquire a surface-illuminance distribution of the incident light on the surface of the subject by using the information about the inclination distribution and an intensity distribution of light for irradiation to the subject,
   set, on the surface of the subject in a numerical space, an imaginary light source having a light intensity distribution that is the same as the surface-illuminance distribution,
   acquire an internal light intensity distribution inside the subject by calculating light propagation inside the subject in the numerical space, of light emitted from the imaginary light source,
   acquire first image data by using the electrical signal, and
   acquire second image data by using the first image data and the internal light intensity distribution inside the subject.

10. The subject information acquisition apparatus according to claim 9, further comprising an image pickup device,
wherein the processing unit is configured to acquire the information about the inclination distribution by using an output from the image pickup device.

11. A subject information acquisition apparatus comprising:
an acoustic-wave converting unit configured to convert an acoustic wave generated by irradiating a subject with light into an electrical signal; and
a processing unit configured to;
acquire a surface-illuminance distribution of the light incident on a surface of the subject by using information about a surface shape of the subject and an intensity distribution of light for irradiation to the subject,
set, on the surface of the subject in a numerical space, an imaginary light source having a light intensity distribution that is the same as the surface-illuminance distribution,
acquire an internal light intensity distribution inside the subject by calculating light propagation inside the subject in the numerical space, of light emitted from the imaginary light source,
acquire first image data using the electrical signal, and
acquire second image data by using the first image data and the internal light intensity distribution inside the subject.

12. The subject information acquisition apparatus according to claim 11, further comprising:
an image pickup device,
wherein the processing unit is configured to acquire the information about the surface shape of the subject by using an output of the image pickup device.

13. The subject information acquisition apparatus according to claim 11, wherein the processing unit is configured to acquire the information about the surface shape of the subject by using the electrical signal.

14. The subject information acquisition apparatus according to claim 11, wherein the processing unit is configured to acquire third image data by using the electrical signal and acquire the information about the surface shape of the subject by using the third image data.

15. The subject information acquisition apparatus according to claim 11, further comprising:
a securing member configured to secure the subject,
wherein the processing unit is configured to acquire the information about the surface shape of the subject based on the securing member.

16. The subject information acquisition apparatus according to claim 11, wherein the processing unit is configured to
hold a plurality of data items of the surface-illuminance distribution of the light incident on the surface of the subject, and
acquire the surface-illuminance distribution of the light incident on the surface of the subject by selecting one of the data items on the basis of the surface shape of the subject.

17. The subject information acquisition apparatus according to claim 11, wherein the surface-illuminance distribution of the light incident on the surface of the subject is determined at various positions based on the surface shape of the subject.

18. The subject information acquisition apparatus according to claim 11, wherein the processing unit is configured to acquire the surface-illuminance distribution of the light incident on the surface of the subject by using information about positions of the surface of the subject as the information about the surface shape of the subject.

19. The subject information acquisition apparatus according to claim 11, wherein the processing unit is configured to acquire the surface-illuminance distribution of the light incident on the surface of the subject by using information about an inclination distribution of the light on the surface of the subject as the information about the surface shape of the subject.

20. The subject information acquisition apparatus according to claim 11, wherein the processing unit is configured to extract parts, as the surface of the subject, having a value greater than a predetermined threshold from the first image data and acquire the information about the surface shape of the subject based on the extracted parts.

21. The subject information acquisition apparatus according to claim 11, wherein the processing unit is configured to acquire an initial sound pressure distribution as the first image data.

22. The subject information acquisition apparatus according to claim 11, wherein the processing unit is configured to acquire an optical-energy-absorption density distribution as the first image data.

23. The subject information acquisition apparatus according to claim 11, wherein the processing unit is configured to acquire an optical absorption-coefficient distribution as the second image data.

24. The subject information acquisition apparatus according to claim 11, further comprising a display unit, wherein the processing unit is configured to cause the display unit to display an image based on the second image data on the display unit.

25. The subject information acquisition apparatus according to claim 11, further comprising a light source, wherein the acoustic-wave converting unit is configured to receive the acoustic wave generated by irradiating the subject with the light from the light source.

26. The subject information acquisition apparatus according to claim 11, wherein the acoustic-wave converting unit is configured to receive the acoustic wave generated inside the subject and at the surface of the subject.

27. The subject information acquisition apparatus according to claim 11, wherein the processing unit is configured acquire an internal light intensity distribution inside the subject by calculating light propagation, of light emitted from the imaginary light source, inside the subject in the numerical space according to a light transport equation, a light diffusion equation, or a Monte Carlo simulation.

28. The subject information acquisition apparatus according to claim 11, wherein an acoustic-wave converting unit includes a transducer using a piezoelectric phenomenon or a transducer using change in capacitance.

29. The subject information acquisition apparatus according to claim 11, further comprising an ultrasonic wave echo acoustic converting unit configured to transmit and receive an acoustic wave, wherein the processing unit is configured to acquire the information about the surface shape of the subject by using an output from the ultrasound wave echo acoustic converting unit.

30. The method according to claim 1, wherein, in acquiring the surface-illuminance distribution, the surface-illuminance distribution is acquired by using information about an inclination distribution of the surface of the subject for incident light onto the surface of the subject as the information about the surface shape of the subject.

31. The method according to claim 1, wherein, in acquiring the surface-illuminance distribution, the surface-illuminance distribution is acquired by using information about positions of the surface of the subject at the surface of the subject as the information about the surface shape of the subject.

32. The method according to claim 1, wherein, in acquiring the internal light intensity distribution, the internal light intensity distribution inside the subject is acquired by calculating light propagation, of light emitted from the imaginary light source, inside the subject in the numerical space according to a light transport equation, a light diffusion equation, or a Monte Carlo simulation.

\* \* \* \* \*